United States Patent
Lee et al.

(10) Patent No.: US 9,952,337 B2
(45) Date of Patent: Apr. 24, 2018

(54) RADIATION DETECTORS, METHODS OF MANUFACTURING THE RADIATION DETECTORS, AND RADIATION IMAGING SYSTEMS INCLUDING THE RADIATION DETECTORS

(71) Applicant: Samsung Electronics Co., Ltd., Suwon-Si, Gyeonggi-Do (KR)

(72) Inventors: Seung-hyup Lee, Yongin-si (KR); Sun-il Kim, Osan-si (KR); Young Kim, Yongin-si (KR); Chang-jung Kim, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 363 days.

(21) Appl. No.: 14/474,214

(22) Filed: Sep. 1, 2014

(65) Prior Publication Data

US 2015/0063543 A1 Mar. 5, 2015

(30) Foreign Application Priority Data

Sep. 2, 2013 (KR) .......................... 10-2013-0105095

(51) Int. Cl.
  *G01T 1/24* (2006.01)
  *H01L 31/032* (2006.01)
  (Continued)

(52) U.S. Cl.
  CPC .............. *G01T 1/24* (2013.01); *G01N 23/04* (2013.01); *G01T 1/2023* (2013.01);
  (Continued)

(58) Field of Classification Search
  CPC .......... G01T 1/24; G01T 1/2023; G01N 23/04
  See application file for complete search history.

(56) References Cited

U.S. PATENT DOCUMENTS

| 5,501,744 A | 3/1996 | Albright et al. |
| 6,398,624 B1 * | 6/2002 | Izumi ........................ B24C 1/00 451/38 |

(Continued)

FOREIGN PATENT DOCUMENTS

| JP | 2003234461 A | * 8/2003 |
| JP | 2010-118602 A | 5/2010 |

(Continued)

OTHER PUBLICATIONS

Apr. 28, 2015, Extended European Search Report issued in corresponding European Patent Application No. 14181618.1.

*Primary Examiner* — Christine Sung

(57) ABSTRACT

A radiation detector may include: a first photoconductor layer including a plurality of photosensitive particles; and/or a second photoconductor layer on the first photoconductor layer, and including a plurality of crystals obtained by crystal-growing photosensitive material. At least some of the plurality of photosensitive particles of the first photoconductor layer may fill gaps between the plurality of crystals of the second photoconductor layer. A method of manufacturing a radiation detector may include: forming a first photoconductor layer by applying paste, including solvent mixed with a plurality of photosensitive particles, to a first substrate; forming a second photoconductor layer by crystal-growing photosensitive material on a second substrate; pressing the crystal-grown second photoconductor layer on the first photoconductor layer that is applied to the first substrate; and/or removing the solvent in the first photoconductor layer via a drying process.

20 Claims, 5 Drawing Sheets

(51) Int. Cl.
| | |
|---|---|
| *H01L 27/146* | (2006.01) |
| *H01L 31/08* | (2006.01) |
| *G01N 23/04* | (2018.01) |
| *G01T 1/202* | (2006.01) |
| *H01L 31/0272* | (2006.01) |
| *H01L 31/028* | (2006.01) |
| *H01L 31/0296* | (2006.01) |
| *H01L 31/0304* | (2006.01) |
| *H01L 31/0336* | (2006.01) |
| *H01L 31/18* | (2006.01) |
| *H01L 31/20* | (2006.01) |
| *H01L 31/0384* | (2006.01) |

(52) U.S. Cl.
CPC .. *H01L 27/14676* (2013.01); *H01L 27/14683* (2013.01); *H01L 31/028* (2013.01); *H01L 31/0272* (2013.01); *H01L 31/0296* (2013.01); *H01L 31/02966* (2013.01); *H01L 31/032* (2013.01); *H01L 31/0304* (2013.01); *H01L 31/0324* (2013.01); *H01L 31/0336* (2013.01); *H01L 31/03845* (2013.01); *H01L 31/085* (2013.01); *H01L 31/18* (2013.01); *H01L 31/1828* (2013.01); *H01L 31/1832* (2013.01); *H01L 31/202* (2013.01)

(56) References Cited

U.S. PATENT DOCUMENTS

| | | | |
|---|---|---|---|
| 8,120,683 B1 * | 2/2012 | Turner | H01L 27/14634 |
| | | | 250/370.09 |
| 9,324,898 B2 * | 4/2016 | Albin | H01L 21/02422 |
| 2001/0010352 A1 | 8/2001 | Teranuma et al. | |
| 2010/0327172 A1 | 12/2010 | Tokuda et al. | |
| 2013/0168563 A1 | 7/2013 | Kim et al. | |

FOREIGN PATENT DOCUMENTS

| | | |
|---|---|---|
| KR | 20050081174 A | 8/2005 |
| KR | 100630236 B1 | 9/2006 |
| KR | 20120084079 A | 7/2012 |
| KR | 20120127909 A | 11/2012 |
| KR | 20130046246 A | 5/2013 |
| KR | 20130076431 A | 7/2013 |

* cited by examiner

RADIATION DETECTORS, METHODS OF MANUFACTURING THE RADIATION DETECTORS, AND RADIATION IMAGING SYSTEMS INCLUDING THE RADIATION DETECTORS

CROSS-REFERENCE TO RELATED APPLICATION(S)

This application claims priority from Korean Patent Application No. 10-2013-0105095, filed on Sep. 2, 2013, in the Korean Intellectual Property Office (KIPO), the entire contents of which are incorporated herein by reference.

BACKGROUND

1. Field

Some example embodiments may relate to radiation detectors, methods of manufacturing the radiation detectors, and/or radiation imaging systems including the radiation detectors. Some example embodiments may relate to radiation detectors including dual-layer structure photoconductor layers, methods of manufacturing the radiation detectors, and/or radiation imaging systems including the radiation detectors.

2. Description of Related Art

In the radiation imaging field using an apparatus such as an X-ray imaging apparatus, in general, a photosensitive film may be exposed to radiation such as an X-ray and then the exposed photosensitive film may be developed so that an image is generated. Recently, a radiation imaging system such as a digital X-ray imaging apparatus has been provided and, in this regard, similar to a general digital camera, the digital X-ray imaging apparatus may detect radiation by using an electro-optical detector, may process an electrical signal from the electro-optical detector, and therefore may generate an image.

A detector used in the radiation imaging system may be required to detect high energy radiation such as an X-ray and, thus, it may be difficult to employ a semiconductor image sensor (e.g., a complementary metal-oxide-semiconductor (CMOS) or charge-coupled device (CCD) image sensor) of the general digital camera that may detect visible rays having relatively low energy. Also, the detector used in the radiation imaging system generally may have large size, which is difficult to manufacture due to costs.

Accordingly, various detectors may be provided with the aim of detecting high energy radiation. For example, a detector for detecting radiation may be manufactured in a manner that a photoconductor layer formed of a photosensitive material including a heavy metal is formed on a substrate.

SUMMARY

Some example embodiments may provide radiation detectors, methods of manufacturing the radiation detectors, and/or radiation imaging systems including the radiation detectors. The radiation detectors may comprise dual-layer structure photoconductor layers.

In some example embodiments, a radiation detector may comprise: a first photoconductor layer comprising a plurality of photosensitive particles; and/or a second photoconductor layer on the first photoconductor layer, and comprising a plurality of crystals obtained by crystal-growing photosensitive material. At least some of the plurality of photosensitive particles of the first photoconductor layer may fill gaps between the plurality of crystals of the second photoconductor layer.

In some example embodiments, the radiation detector may further comprise: a first substrate; and/or an array of a plurality of pixel electrodes on the first substrate. The first photoconductor layer may cover the plurality of pixel electrodes on the first substrate.

In some example embodiments, the first photoconductor layer may comprise paste, including solvent mixed with the plurality of photosensitive particles, applied to the first substrate.

In some example embodiments, the first substrate may be formed of insulating material.

In some example embodiments, the radiation detector may further comprise a common electrode on the second photoconductor layer.

In some example embodiments, the second photoconductor layer may comprise crystal-grown, vaporized photosensitive material.

In some example embodiments, the second photoconductor layer formed on the second substrate may comprise: a first surface in which a plurality of pores are formed among the plurality of crystals; and/or a flat second surface that contacts the second substrate.

In some example embodiments, the first surface of the second photoconductor layer may contact the first photoconductor layer.

In some example embodiments, the second substrate may be formed of conductive material.

In some example embodiments, each of the plurality of photosensitive particles of the first photoconductor layer may comprise $HgI_2$ or Se. Each of the plurality of crystals of the second photoconductor layer may comprise $HgI_2$ or Se.

In some example embodiments, a radiation imaging system may comprise: a radiation emitting device configured to emit radiation; a radiation detector configured to output an electrical signal by detecting the radiation emitted from the radiation emitting device; and/or an image signal processing unit configured to generate an image from the electrical signal output from the radiation detector. The radiation detector may comprise: a first photoconductor layer comprising a plurality of photosensitive particles; and/or a second photoconductor layer on the first photoconductor layer, and comprising a plurality of crystals obtained by crystal-growing photosensitive material. At least some of the plurality of photosensitive particles of the first photoconductor layer may fill gaps between the plurality of crystals of the second photoconductor layer.

In some example embodiments, a method of manufacturing a radiation detector may comprise: forming a first photoconductor layer by applying paste, comprising solvent mixed with a plurality of photosensitive particles, to a first substrate; forming a second photoconductor layer by crystal-growing photosensitive material on a second substrate; pressing the crystal-grown second photoconductor layer on the first photoconductor layer that is applied to the first substrate; and/or removing the solvent in the first photoconductor layer via a drying process.

In some example embodiments, the forming of the first photoconductor layer may comprise: forming an array of a plurality of pixel electrodes on the first substrate; and/or applying the paste to the first substrate so as to cover the plurality of pixel electrodes.

In some example embodiments, the first substrate may comprise insulating material.

In some example embodiments, the forming of the second photoconductor layer may comprise: crystal-growing vaporized photosensitive material on the second substrate.

In some example embodiments, the second photoconductor layer may comprise: a first surface that includes a plurality of pores among the plurality of crystals; and/or a flat second surface that contacts the second substrate.

In some example embodiments, the pressing may comprise allowing the first surface of the second photoconductor layer to contact the first photoconductor layer, whereby at least some of the plurality of photosensitive particles of the first photoconductor layer may fill gaps between the plurality of crystals of the second photoconductor layer.

In some example embodiments, the second substrate may comprise conductive material configured to function as a common electrode.

In some example embodiments, the method may further comprise: removing the second substrate from the second photoconductor layer; and/or forming a common electrode on a surface of the second photoconductor layer that contacted the second substrate.

In some example embodiments, each of the plurality of photosensitive particles of the first photoconductor layer may comprise $HgI_2$ or Se. The photosensitive material of the second photoconductor layer may comprise $HgI_2$ or Se.

In some example embodiments, a radiation detector may comprise: a first photoconductor layer comprising photosensitive particles; and/or a second photoconductor layer comprising crystal-grown, photosensitive-material crystals. At least some of the photosensitive particles may fill gaps between the crystals.

In some example embodiments, the radiation detector may further comprise a first substrate. The first substrate may contact the first photoconductor layer.

In some example embodiments, the first substrate may comprise insulating material.

In some example embodiments, the radiation detector may further comprise: a first substrate; and/or pixel electrodes on the first substrate. The first photoconductor layer may cover the pixel electrodes.

In some example embodiments, the pixel electrodes may form a two-dimensional array on the first substrate.

In some example embodiments, the radiation detector may further comprise a second substrate. The second substrate may contact the second photoconductor layer.

In some example embodiments, the second substrate may comprise insulating material.

In some example embodiments, the second substrate may comprise conductive material.

BRIEF DESCRIPTION OF THE DRAWINGS

The above and/or other aspects and advantages will become more apparent and more readily appreciated from the following detailed description of example embodiments, taken in conjunction with the accompanying drawings, in which.

DETAILED DESCRIPTION

Figure 1A:
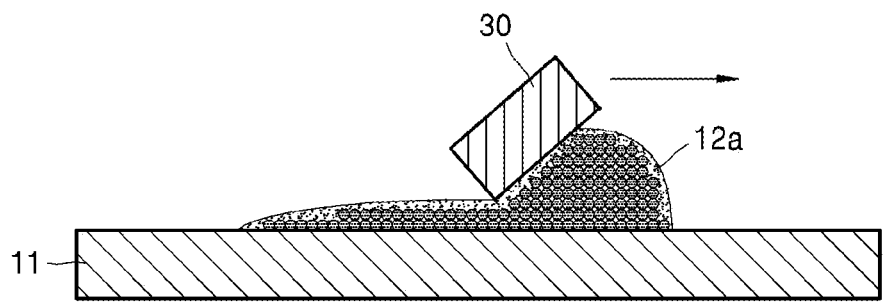
FIGS. 1A through 1E illustrate a method of forming a dual-layer structure photoconductor layer according to some example embodiments.

Example embodiments will now be described more fully with reference to the accompanying drawings. Embodiments, however, may be embodied in many different forms and should not be construed as being limited to the embodiments set forth herein. Rather, these example embodiments are provided so that this disclosure will be thorough and complete, and will fully convey the scope to those skilled in the art. In the drawings, the thicknesses of layers and regions may be exaggerated for clarity.

It will be understood that when an element is referred to as being "on," "connected to," "electrically connected to," or "coupled to" to another component, it may be directly on, connected to, electrically connected to, or coupled to the other component or intervening components may be present. In contrast, when a component is referred to as being "directly on," "directly connected to," "directly electrically connected to," or "directly coupled to" another component, there are no intervening components present. As used herein, the term "and/or" includes any and all combinations of one or more of the associated listed items.

It will be understood that although the terms first, second, third, etc., may be used herein to describe various elements, components, regions, layers, and/or sections, these elements, components, regions, layers, and/or sections should not be limited by these terms. These terms are only used to distinguish one element, component, region, layer, and/or section from another element, component, region, layer, and/or section. For example, a first element, component, region, layer, and/or section could be termed a second element, component, region, layer, and/or section without departing from the teachings of example embodiments.

Spatially relative terms, such as "beneath," "below," "lower," "above," "upper," and the like may be used herein for ease of description to describe the relationship of one component and/or feature to another component and/or feature, or other component(s) and/or feature(s), as illustrated in the drawings. It will be understood that the spatially relative terms are intended to encompass different orientations of the device in use or operation in addition to the orientation depicted in the figures.

The terminology used herein is for the purpose of describing particular example embodiments only and is not intended to be limiting of example embodiments. As used herein, the singular forms "a," "an," and "the" are intended to include the plural forms as well, unless the context clearly indicates otherwise. It will be further understood that the terms "comprises," "comprising," "includes," and/or "including," when used in this specification, specify the presence of stated features, integers, steps, operations, elements, and/or components, but do not preclude the presence or addition of one or more other features, integers, steps, operations, elements, components, and/or groups thereof.

Example embodiments may be described herein with reference to cross-sectional illustrations that are schematic illustrations of idealized example embodiments (and intermediate structures). As such, variations from the shapes of the illustrations as a result, for example, of manufacturing techniques and/or tolerances, are to be expected. Thus, example embodiments should not be construed as limited to the particular shapes of regions illustrated herein but are to include deviations in shapes that result, for example, from manufacturing. For example, an implanted region illustrated as a rectangle will typically have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature, their shapes are not intended to illustrate the actual shape of a region of a device, and their shapes are not intended to limit the scope of the example embodiments.

Unless otherwise defined, all terms (including technical and scientific terms) used herein have the same meaning as commonly understood by one of ordinary skill in the art to which example embodiments belong. It will be further understood that terms, such as those defined in commonly used dictionaries, should be interpreted as having a meaning that is consistent with their meaning in the context of the relevant art and should not be interpreted in an idealized or overly formal sense unless expressly so defined herein.

Reference will now be made to example embodiments, which are illustrated in the accompanying drawings, wherein like reference numerals may refer to like components throughout.

FIGS. 1A through 1E illustrate a method of forming a dual-layer structure photoconductor layer according to some example embodiments.

Referring to FIG. 1A, a paste 12a is arranged by mixing a solvent, a binder, and a plurality of fine photosensitive particles capable of detecting high energy radiation. Each of the photosensitive particles may be formed of mercury (II) iodide ($HgI_2$), selenium (Se), $PbI_2$, CdTe, CdZnTe, PbO, TlBr, a-Si or the like and may have a diameter between about 1 μm and about 10 μm. Also, polyvinyl butyral (PVB), poly-propylene (PP), poly-ethylene (PE), poly-styrene (PS), or acrylonitrile-butadiene-styrene (ABS) may be used as the binder, and a material such as diethylene glycol monobutyl ether (DGME), cyclohexanone, xylene having a sufficient viscosity to ensure that the paste 12a is not free-flowing may be used as the solvent.

Figure 1B:
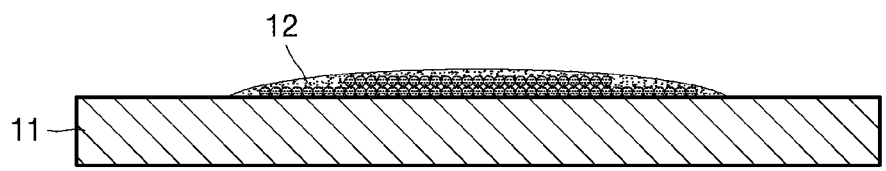

Afterward, the paste 12a may be disposed on a substrate 11 and/or may be spread by using a squeegee 30 (or similar device), so that the paste 12a may be broadly coated with an approximately consistent thickness on a surface of the substrate 11. Then, as illustrated in FIG. 1B, a first photoconductor layer 12 having an approximately consistent thickness may be formed on the substrate 11.

The aforementioned process, in which the paste 12a including the plurality of fine photosensitive particles is applied to the substrate 11, may be referred as a particle in binder (PIB) process. In general, a first photoconductor layer 12 formed via the PIB process may have excellent uniformity. However, because the first photoconductor layer 12 may be formed of very small photosensitive particles, a movement path of electrons and holes formed due to incident radiation may be complicated, and a mobility of the electrons and holes may be less than desired. Due to that, the first photoconductor layer 12 formed via the PIB process may have low sensitivity.

Figure 1C:
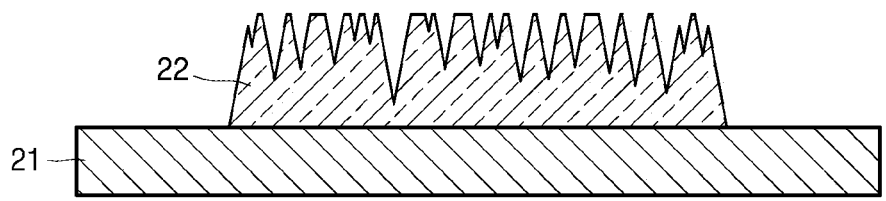

Thus, in order to supplement the relatively low sensitivity of the first photoconductor layer 12, as illustrated in FIG. 1C, a second photoconductor layer 22 may be separately formed. For example, the second photoconductor layer 22 may be formed in a manner that a photosensitive material is vaporized and then the vaporized photosensitive material is crystal grown on a substrate 21 that is different from the substrate 11 of the first photoconductor layer 12. The aforementioned crystal-growing method may be performed by using a physical vapor deposition (PVD) process. In general, the second photoconductor layer 22 formed by using the crystal growing method may have a crystal structure where electrons and holes have high mobility. However, compared to the first photoconductor layer 12 formed via the PIB process, the second photoconductor layer 22 may have low thickness uniformity and/or may have pores among crystals, such that resolution of an image may be less than desired.

Figure 1D:
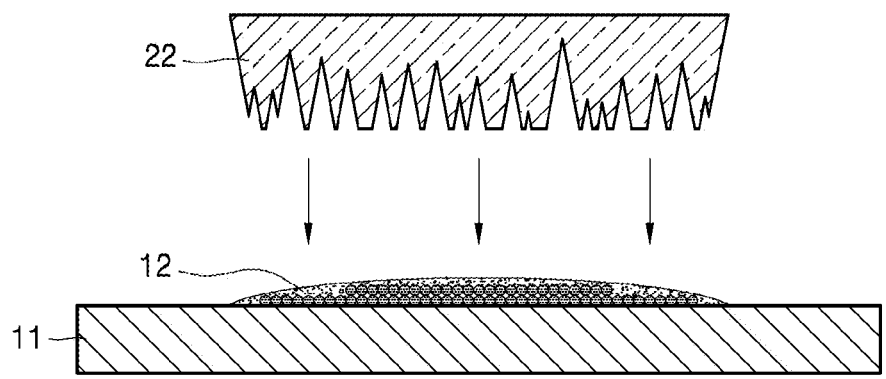

According to some example embodiments, in order to mutually supplement characteristics of the first photoconductor layer 12 and the second photoconductor layer 22, as illustrated in FIG. 1D, the second photoconductor layer 22 may be disposed on the first photoconductor layer 12. For example, the second photoconductor layer 22 may be reversed and then may be disposed on the first photoconductor layer 12, so that a top surface of the second photoconductor layer 22, which has the pores, may contact the first photoconductor layer 12, and a flat bottom surface (e.g., a surface that contacts the substrate 21) of the second photoconductor layer 22 may face upward. Referring to FIG. 1D, the second photoconductor layer 22 may be removed from the substrate 21. However, example embodiments are not limited thereto, and the second photoconductor layer 22 may be disposed on the first photoconductor layer 12 without removing the substrate 21 from the second photoconductor layer 22. In a case where the substrate 21 is not removed, in FIG. 1D, the substrate 21 may be disposed above the second photoconductor layer 22.

Figure 1E:
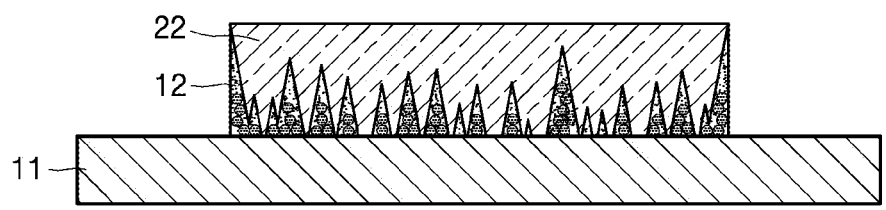

After the second photoconductor layer 22 is disposed on the first photoconductor layer 12, as illustrated in FIG. 1E, the second photoconductor layer 22 may be pressed against the first photoconductor layer 12 so as to allow the photosensitive particles of the first photoconductor layer 12 to fill the pores of the second photoconductor layer 22. After the second photoconductor layer 22 is pressed on the first photoconductor layer 12, the solvent remaining in the first photoconductor layer 12 may be removed via a drying process. For example, the drying process may be performed at a temperature of about 80° C. in an oven. By doing so, the dual-layer structure photoconductor layer may be formed. The dual-layer structure photoconductor layer may comprise, for example, second photoconductor layer 22 on first photoconductor layer 12.

Figure 2:
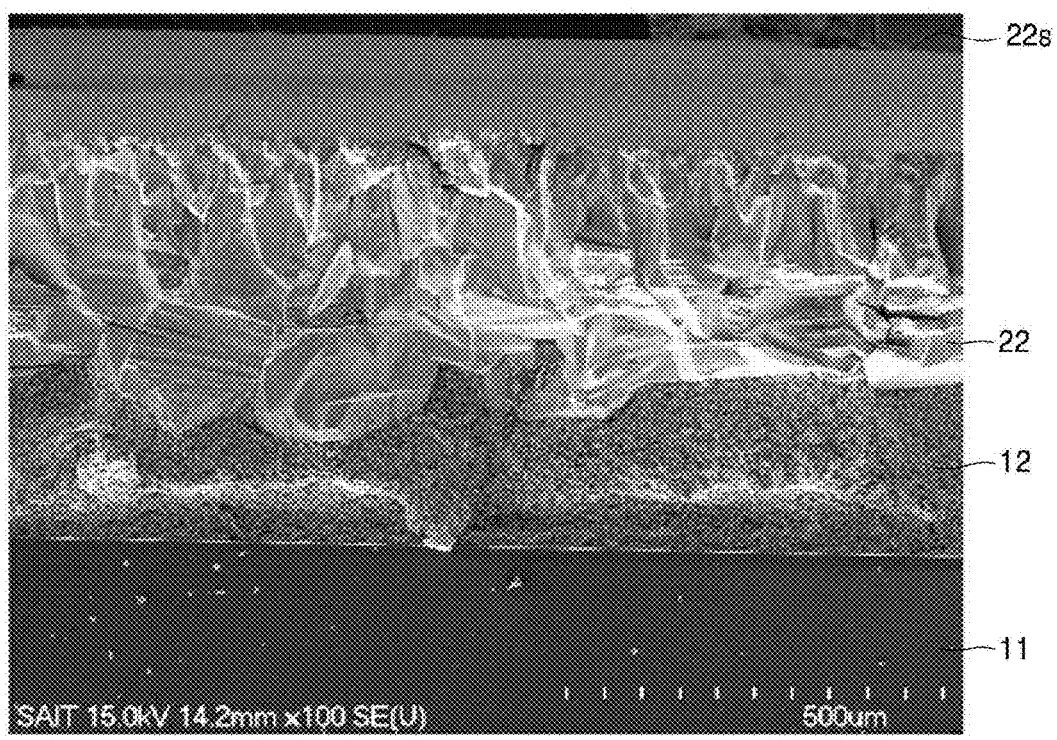
FIG. 2 is an image of a cross-section of the dual-layer structure photoconductor layer formed by using the method shown in FIGS. 1A through 1E.

FIG. 2 is an image of a cross-section of the dual-layer structure photoconductor layer formed by using the method described with reference to FIGS. 1A through 1E. Referring to FIG. 2, the first photoconductor layer 12 and the second photoconductor layer 22 may be sequentially disposed on the substrate 11, and portions of the first photoconductor layer 12 may almost completely fill gaps between the crystals of the second photoconductor layer 22. A surface 22s of the second photoconductor layer 22 may be very flat. This is because the surface 22s of the second photoconductor layer 22 shown in FIG. 2 may actually be the bottom surface that contacts the substrate 21 and/or from which the crystal growth begins. The dual-layer structure photoconductor layer may comprise, for example, second photoconductor layer 22 on first photoconductor layer 12, and first photoconductor layer 12 on substrate 11.

As shown in the image of FIG. 2, the dual-layer structure photoconductor layer formed by using the method described with reference to FIGS. 1A through 1E may have a flat top surface and a flat bottom surface, may have an approximately consistent thickness, and/or may have a structure in which the photosensitive materials are distributed in a relatively uniform way. Also, the dual-layer structure photoconductor layer may have electrons and holes having high mobility due to the crystal structure of the second photoconductor layer 22. Thus, it may be possible to simultaneously obtain an excellent uniformity and high mobility, so that a large-size radiation detector having a high sensitivity and excellent image resolution may be manufactured.

Figure 3A:
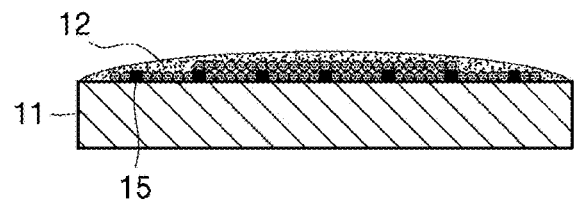
FIGS. 3A through 3C illustrate a method of manufacturing a radiation detector by using the method of forming a dual-layer structure photoconductor layer according to some example embodiments.
Figure 3B:
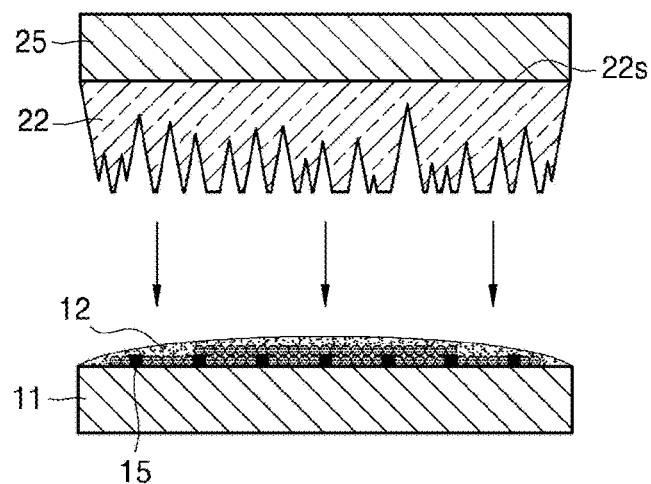
Figure 3C:
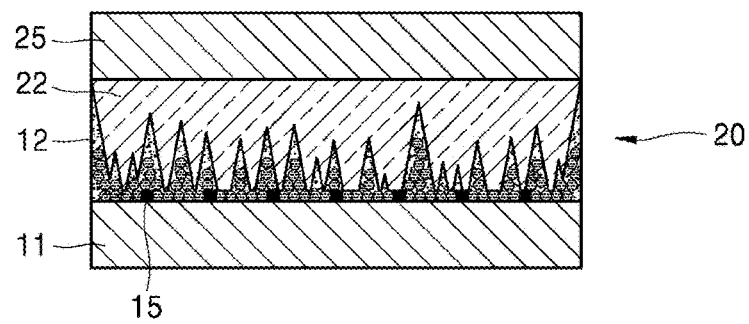

FIGS. 3A through 3C illustrate a method of manufacturing a radiation detector 20 by using the method of forming a dual-layer structure photoconductor layer, according to some example embodiments.

First, referring to FIG. 3A, a plurality of pixel electrodes 15 may be formed on the substrate 11, and according to the PIB process shown in FIGS. 1A and 1B, the first photoconductor layer 12 may be applied to the substrate 11 so as to cover the plurality of pixel electrodes 15. For example, the plurality of pixel electrodes 15 may be arranged at regular intervals in, for example, a two-dimensional (2D) array on a surface (e.g., some or all of a top surface) of the substrate 11. For example, the substrate 11 may be formed of insulating material.

Referring to FIG. 3B, according to a process shown in FIGS. 1C and 1D, the second photoconductor layer 22 may be formed by crystal-growing a photosensitive material on the substrate 21 by using a PVD or chemical vapor deposition (CVD) process, and then the crystal-grown second photoconductor layer 22 may be pressed on the first photoconductor layer 12. Then, photosensitive particles of the first photoconductor layer 12 may fill pores of the second photoconductor layer 22.

For example, a common electrode 25 may be attached to the surface 22s of the second photoconductor layer 22. For example, the substrate 21 for growing the second photoconductor layer 22 may be used as the common electrode 25. In this case, in order to function as the common electrode 25, the substrate 21 may be formed of conductive material such as metal. When the substrate 21 is formed of a conductive material, the second photoconductor layer 22 may be pressed on the first photoconductor layer 12 while the substrate 21 is still attached to the second photoconductor layer 22.

Alternatively, the substrate 21 may be formed of insulating material. When the substrate 21 is formed of insulating material, the substrate 21 may be removed from the second photoconductor layer 22, the common electrode 25 may be attached to the surface 22s (e.g., a surface to which the substrate 21 was attached) of the second photoconductor layer 22, and then the second photoconductor layer 22 may be pressed on the first photoconductor layer 12. Alternatively, orders of a procedure of attaching the common electrode 25 to the second photoconductor layer 22 and a procedure of pressing the second photoconductor layer 22 on the first photoconductor layer 12 may be switched. For example, the second photoconductor layer 22 may be first pressed on the first photoconductor layer 12, and then the common electrode 25 may be attached to the surface 22s of the second photoconductor layer 22.

Afterward, once the solvent remaining in the first photoconductor layer 12 is removed via a drying process, the radiation detector 20 as shown in FIG. 3C may be manufactured. If the common electrode 25 that is separate from the substrate 21 is used, a time to perform the drying process may be variously selected. For example, after the second photoconductor layer 22 is pressed on the first photoconductor layer 12 and the drying process is performed, the common electrode 25 may be attached to the surface 22s of the second photoconductor layer 22. Alternatively, after the second photoconductor layer 22 is pressed on the first photoconductor layer 12 and the common electrode 25 is attached to the surface 22s of the second photoconductor layer 22, the drying process may be performed.

Referring to FIG. 3C, the radiation detector 20 may include the substrate 11; the array of the plurality of pixel electrodes 15 formed on the substrate 11; the first photoconductor layer 12 that is formed on the substrate 11 so as to cover the plurality of pixel electrodes 15 and that includes the plurality of fine photosensitive particles; the second photoconductor layer 22 that is disposed on the first photoconductor layer 12 and that includes crystals obtained by crystal growing the photosensitive materials; and/or the common electrode 25 disposed on the second photoconductor layer 22. For example, at least some of the photosensitive particles of the first photoconductor layer 12 may fill gaps between the crystals of the second photoconductor layer 22. As described above, the radiation detector 20 according to some example embodiments may have a high sensitivity and excellent image resolution. The radiation detector 20 may comprise, for example, common electrode 25 on second photoconductor layer 22, second photoconductor layer 22 on first photoconductor layer 12, and first photoconductor layer 12 on substrate 11.

Figure 4:
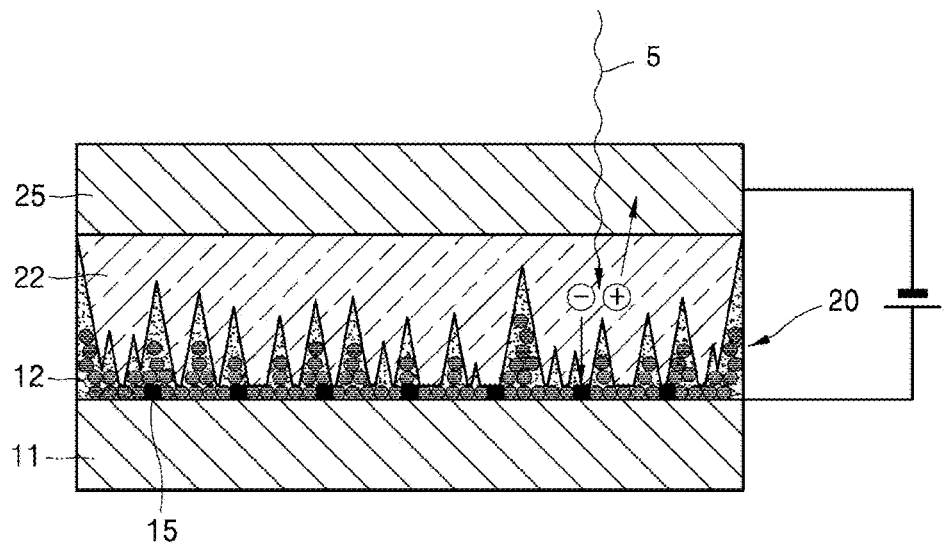
FIG. 4 is a cross-sectional view illustrating an operation of the radiation detector shown in FIG. 3C.

FIG. 4 is a cross-sectional view illustrating an operation of the radiation detector 20 shown in FIG. 3C. In FIG. 4, it is assumed that the common electrode 25 is a negative electrode and each of the pixel electrodes 15 is a positive electrode (but the signs of the electrodes may be reversed). For example, when radiation 5 such as an X-ray having a high energy is incident on the radiation detector 20, an electron and a hole are generated in the first photoconductor layer 12 or the second photoconductor layer 22 which is within an incident region of the radiation 5. According to a position at which the radiation 5 is absorbed, the electron and hole may be generated in at least one or both of the first photoconductor layer 12 and the second photoconductor layer 22. The electron and hole may move in opposite directions along an electric field formed between the common electrode 25 and the pixel electrodes 15. For example, when the common electrode 25 is a negative electrode and each of the pixel electrodes 15 is a positive electrode, the hole may move toward the common electrode 25, and the electron may move toward the closest pixel electrode 15 from among the pixel electrodes 15. Thus, when an electron is detected (e.g., when current is increased) at one pixel electrode 15 from among the pixel electrodes 15, it may be possible to detect that the radiation 5 was incident on or near a position of the one pixel electrode 15. The radiation detector 20 may comprise, for example, common electrode 25 on second photoconductor layer 22, second photoconductor layer 22 on first photoconductor layer 12, first photoconductor layer 12 on pixel electrodes 15 and substrate 11, and pixel electrodes 15 on substrate 11. A voltage may be applied across second photoconductor layer 22 and first photoconductor layer 12 using, for example, common electrode 25 and substrate 11. The polarity of the voltage may be the same as that shown in FIG. 4 or opposite to that shown in FIG. 4.

Figure 5:
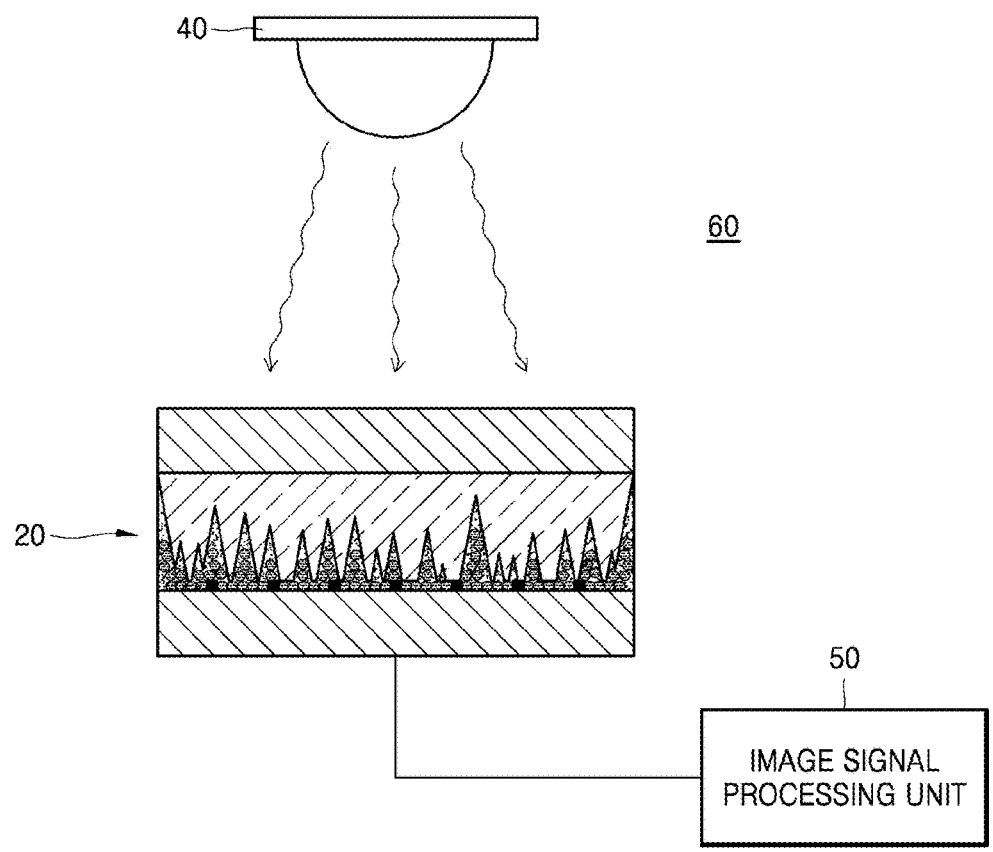
FIG. 5 illustrates a structure of a radiation imaging system including the radiation detector shown in FIG. 3C, according to some example embodiments.

FIG. 5 illustrates a structure of a radiation imaging system 60 including the radiation detector 20 shown in FIG. 3C, according to some example embodiments. Referring to FIG. 5, the radiation imaging system 60 may include a radiation emitting device 40 for emitting high energy radiation such as an X-ray, the radiation detector 20 shown in FIG. 3C, and/or an image signal processing unit 50 for generating an image.

The radiation detector 20 may output electrical signals by detecting the high energy radiation emitted from the radiation emitting device 40. Although not illustrated, a sample may be disposed between the radiation emitting device 40 and the radiation detector 20. The radiation detector 20 may detect, for example, radiation that passes through the sample or that is diffracted or refracted due to the sample, and may electrically output a result of the detection. The image signal processing unit 50 may generate a visibly recognizable image by using the electrical signal output from the radiation detector 20.

The radiation detector, the method of manufacturing the radiation detector, and the radiation imaging system including the radiation detector are described above according to exemplary embodiments with reference to the accompanying drawings. It should be understood that the exemplary embodiments described herein should be considered in a descriptive sense only and not for purposes of limitation. Descriptions of features or aspects within each embodiment should typically be considered as available for other similar features or aspects in other embodiments.

What is claimed is:

1. A radiation detector, comprising:
a first photoconductor layer comprising photosensitive particles; and
a second photoconductor layer comprising crystal-grown, photosensitive-material crystals,
wherein the photosensitive-material crystals comprise one or more gaps, each of the one or more gaps including a plurality of the photosensitive particles,
wherein the photosensitive particles are deposited in gaps between the photosensitive-material crystals by a paste comprising a solvent mixed with the photosensitive particles, wherein the paste is applied to a first substrate.

2. The radiation detector of claim 1, further comprising:
the first substrate; and
an array of a plurality of pixel electrodes on the first substrate,
wherein the first photoconductor layer covers the plurality of pixel electrodes on the first substrate and contacts the first substrate.

3. The radiation detector of claim 2, wherein the first substrate comprises insulating material.

4. The radiation detector of claim 1, further comprising: a common electrode on the second photoconductor layer.

5. The radiation detector of claim 1, further comprising:
a second substrate, wherein the second substrate contacts the second photoconductor layer.

6. The radiation detector of claim 5, wherein the second photoconductor layer comprises:
a first surface that includes a plurality of pores among the photosensitive-material crystals; and
a flat second surface that contacts the second substrate.

7. The radiation detector of claim 6, wherein the first surface of the second photoconductor layer contacts the first photoconductor layer.

8. The radiation detector of claim 6, wherein the second substrate comprises conductive material.

9. The radiation detector of claim 1, wherein each of the photosensitive particles of the first photoconductor layer comprises $HgI_2$, Se, $PbI_2$, CdTe, CdZnTe, PbO, TlBr, or a-Si, and wherein each of the photosensitive-material crystals of the second photoconductor layer comprise $HgI_2$, Se, $PbI_2$, CdTe, CdZnTe, PbO, TlBr, or a-Si.

10. The radiation detector of claim 1, wherein at least some of the photosensitive particles completely fill a plurality of gaps between the photosensitive-material crystals and wherein two or more of the photosensitive particles completely fill a first gap in the photosensitive-material crystals.

11. A radiation imaging system, comprising:
a radiation emitting device configured to emit radiation;
a radiation detector configured to output an electrical signal by detecting the radiation emitted from the radiation emitting device; and
an image signal processing unit configured to generate an image from the electrical signal output from the radiation detector,
wherein the radiation detector comprises:
a first photoconductor layer comprising a plurality of photosensitive particles; and
a second photoconductor layer on the first photoconductor layer, the second photoconductor layer comprising a plurality of crystals obtained by crystal-growing photosensitive material,
wherein the photosensitive-material crystals comprise one or more gaps, each of the one or more gaps comprise a plurality of the photosensitive particles such that a first gap includes a first plurality of photosensitive particles and a second gap includes a second plurality of photosensitive particles, and
wherein the photosensitive particles are deposited in gaps between the photosensitive-material crystals by a paste comprising a solvent mixed with the photosensitive particles, wherein the paste is applied to a first substrate.

12. A method of manufacturing a radiation detector, the method comprising:
forming a first photoconductor layer by applying paste, comprising solvent mixed with a plurality of photosensitive particles, to a first substrate;
forming a second photoconductor layer by crystal-growing photosensitive material on a second substrate;
pressing the crystal-grown second photoconductor layer on the first photoconductor layer that is applied to the first substrate; and
removing the solvent in the first photoconductor layer via a drying process.

13. The method of claim 12, wherein the forming of the first photoconductor layer comprises:
forming an array of a plurality of pixel electrodes on the first substrate; and
applying the paste to the first substrate so as to cover the plurality of pixel electrodes.

14. The method of claim 12, wherein the first substrate comprises insulating material.

15. The method of claim 12, wherein the forming of the second photoconductor layer comprises:
crystal-growing vaporized photosensitive material on the second substrate.

16. The method of claim 15, wherein the second photoconductor layer formed on the second substrate comprises:
a first surface in which a plurality of pores are formed among a plurality of crystals of the crystal-grown second photoconductor layer; and
a flat second surface that contacts the second substrate.

17. The method of claim 16, wherein the pressing comprises allowing the first surface of the second photoconductor layer to contact the first photoconductor layer, whereby at least some of the plurality of photosensitive particles of the first photoconductor layer fill gaps between the plurality of crystals of the second photoconductor layer.

18. The method of claim 15, wherein the second substrate comprises conductive material configured to function as a common electrode.

19. The method of claim 12, further comprising:
    removing the second substrate from the second photoconductor layer; and
    forming a common electrode on a surface of the second photoconductor layer that contacted the second substrate.

20. The method of claim 12, wherein each of the plurality of photosensitive particles of the first photoconductor layer comprises $HgI_2$, Se, $PbI_2$, CdTe, CdZnTe, PbO, TlBr, or a-Si, and
    wherein the photosensitive material of the second photoconductor layer comprises $HgI_2$, Se, $PbI_2$, CdTe, CdZnTe, PbO, TlBr, or a-Si.

* * * * *